US00PP08893P

United States Patent [19]

Drewlow

[11] Patent Number: Plant 8,893

[45] Date of Patent: Sep. 13, 1994

[54] IMPATIENS PLANT NAMED MINUET

[75] Inventor: Lyndon W. Drewlow, Ashtabula, Ohio

[73] Assignee: Mikkelsens, Inc., Ashtabula, Ohio

[21] Appl. No.: 163,766

[22] Filed: Dec. 9, 1993

[51] Int. Cl.[5] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Foley & Lardner

[57] ABSTRACT

A new and distinct cultivar of Impatiens plant named Minuet, charcterized by its double-flower form with ten petals, salmon-pink flower color, relative large diameter flowers carried on green pedicels, solid deep green leaves, later flowering habit due to double flower form, highly self-branching and floriferous habits, tolerance to both high and cool temperatures, and its adaptability to be grown in 10 cm up to 15–25 cm containers.

1 Drawing Sheet

The present invention relates to a new and distinctive cultivar of Impatiens plant, botanically known as Impatiens, commercially known as New Guinea Impatiens, and known by the cultivar name Minuet.

The new culture was developed in a controlled breeding program conducted by the inventor Lyndon W. Drewlow in Ashtabula, Ohio. Minuet was created by crossing Mikkelsen Seedling No. 90-133-3 (seed parent) with Mikkelsen Seedling No. 90-124-2 (pollen parent). Both parents are proprietary cultivars used in the breeding program.

Asexual reproduction by terminal or stem cuttings carried out by or under the supervision of the inventor at Ashtabula, Ohio has shown that the unique features of this new impatiens are stabilized and are reproduced true to type in successive propagations.

The following combination of characteristics distinguish the new impatiens from both its parent varieties and other cultivated impatiens of this type known and used in the floriculture industry. The description includes reference to comparison cultivars Quasar, disclosed in U.S. Plant Pat. No. 5,780 and Largo, disclosed in a pending application of the inventor.

1. Minuet is a representative of an entirely new class of New Guinea impatiens that have ten (10) flower petals, which is double the number of petals of the single flower type such as Quasar which has five (5) petals. Largo is another cultivar in the double-flavored group.

2. Minuet is salmon-pink in flower color (54B) while Quasar is salmon-orange (41C), maturing to 40D.

3. Minuet has a larger diameter flower (5.5 to 6.0 cm) than Quasar (5.0 cm) but is similar in flower diameter to Largo.

4. Minuet has green flower pedicels while Quasar has a reddish cast to the entire pedicel and Largo has green flower pedicels with a reddish cast near the end where attached to the flower.

5. Minuet has solid green leaves like Largo, while Quasar has green leaves with cream variegation around the midrib, especially at the basal end of the leaf.

6. Minuet has longer, narrower leaves (10 to 11 cm long and 3.0 to 3.5 cm wide) compared to the leaves of Quasar which are 6.0 to 6.5 cm long and 3.5 to 3.75 cm wide, and the leaves of Largo which are 8.5 to 9.5 cm long and 3.5 to 4.0 cm wide.

7. The upper leaf surface of Minuet is glabrous, as is Largo, but Quasar has a hirsute upper leaf surface.

8. Minuet is 3 to 5 days later to bloom than Quasar as it takes the ten (10) petal double flower longer to develop and open than the five (5) petals of the single-flowered Quasar. Minuet is similar in bloom date to Largo.

9. Minuet is much more self-branched than Quasar with Largo being similar to Minuet in degree of self-branching. The self-branching characteristic eliminates the need for apical meristem removal for high degree of branching thus reducing production time by four (4) weeks or more.

10. Flower spur on mature bud of Minuet is 4.0 cm in length, longer than the 3.75 cm spur of Quasar but shorter than the 4.5 cm spur of Largo.

In the photographic drawings, the color photo at the top illustrates in perspective view the overall appearance of Minuet, with colors being as true as it is reasonably possible to obtain in a color reproduction of this type. The color photo was taken on Sep. 24, 1993 under natural light under 40% saran in a shaded glass greenhouse in Ashtabula, Ohio on a sunny day. The black and white photo on the bottom of the sheet shows three (3) views of a typical flower of the new cultivar.

The following is a detailed description of Minuet, based on plants produced in greenhouses in Ashtabular, Ohio during the summer season of the year. Plants were grown in 15 cm pots and measurements were taken 18 weeks after rooted cuttings were planted. Height measurements were taken from the soil line of the container. The plants were grown at 65°–68° F. night temperatures under 3000–4000 foot candles of light, and 250 ppm nitrogen, 75 ppm potassium, and 250 ppm phosphorous nutritional levels, with trace elements added. The habit of growth, foliage coloration, leaf variegation, size of leaves and flower size will be influenced by nutritional and environmental conditions, without, however, any variation in the genotype.

Color references are made to The Royal Horticultural Society Colour Chart except where general terms of ordinary dictionary significance are used.

Parentage: A controlled cross between female parent Mikkelsen Seedling No. 90-113-3 and male parent Mikkelsen Seedling No. 90-124-2.

Propagation:

(A) *Type cutting.*—Stem tip 15 mm long will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit of growth.*—Semi-upright; self-branched, intermediate in height, flowers above leaf canopy; continuous flowering; vigorous growing herb.

(B) *Foliage.*—Bright green with reddish tint to midrib on mature leaves, with immature leaves having a yellow-green midrib; no variegation. (1) Size: 10 to 11 cm long and 3.0 to 3.5 cm wide for average mature leaf. (2) Shape: Lanceolate with acuminate apex and acute base. (3) Texture: Both upper and lower surfaces are glabrous. (4) Margin: Finely serrated with fine ciliate. (5) Color: Young foliage, top side is 146B; under side is 146C; mature foliage, top side is 147A; under side is 147C. (6) Veination: Pinnate, green veins.

Flowering description:

(A) *Flowering habit.*—Flowering continuously from leaf whorl in a progressively orderly manner, with one flower per leaf axil. However, occasionally there can be two flowers per leaf axil. When the last flower in a leaf whorl opens, the first flower in the leaf whorl above starts to open. it takes 5 to 7 days for a mature bud to fully open and the flower may last two weeks or longer depending on the environment.

(B) *Natural flowering season.*—Indeterminant and continuous; quantity of flowering increases with increasing levels of light.

(C) *Flower buds.*—Ellipsoidal, flowers perfect; reddish purple cast to 4.0 cm long spur with green tip on mature bud. Throat is behind the ovary and originates from the major sepal.

(D) *Flowers borne.*—On individual green pedicels 3.5 to 4.0 cm long from whorl of usually five (5) leaves, flowering progressively around the whorl as buds and leaves develop. One flower per leaf axil is normal.

(E) *Quantity of flowers.*—Highly floriferous because of self-branching nature of plant, long-lasting flowers and full appearance of double flowers.

(F) *Diameter of flower.*—5.5 to 6.0 cm.

(G) *Petals.*—(1) Shape: Heart, keel of bottom whorl of petals is largest. (2) Color: Top side in summer when opening is 54B, fading to 63C; under side is 54C. (3) Number of petals: 10. (4) Type of petals: Lower whorl has a true standard petal while upper whorl has a semi-standard petal. Wings are two sets of wing petals. Keels are two sets of keel petals.

(H) *Reproductive organs.*—(1) Stamens: Five (5) in number. (a) Anther: Hooded shape; color is cream with reddish tint on top of hood. (b) Pollen color: Cream. (2) Pistels: (a) Stigma shape: Five (5), segmented column; color is greenish-white. (b) Style color: Greenish white. (c) Ovaries: Five (5) in number; size is 5 mm; color is green when mature.

Disease resistance: No significant disease or insect problems to date.

OTHER IMPORTANT CHARACTERISTICS

1. Self-branching characteristic and semi-upright and intermediate height of Minuet make it suitable for 10 cm pot production, but the plant is vigorous enough for 15 and 25 cm pot production as well.

2. Minuet can withstand both high temperatures and sunlight as well as low temperatures (40° to 50° F.), thus extending the outside growing season outdoors and locations it can be planted.

3. The ten (10) flower petals result in a fuller looking flower as compared to the normal five (5) petals. A double-flowered plant with the same number of flowers as a single-flowered plant will therefore appear substantially more colorful.

I claim:

1. A new and distinct cultivar of Impatiens plant named Minuet, as illustrated and described.

* * * * *

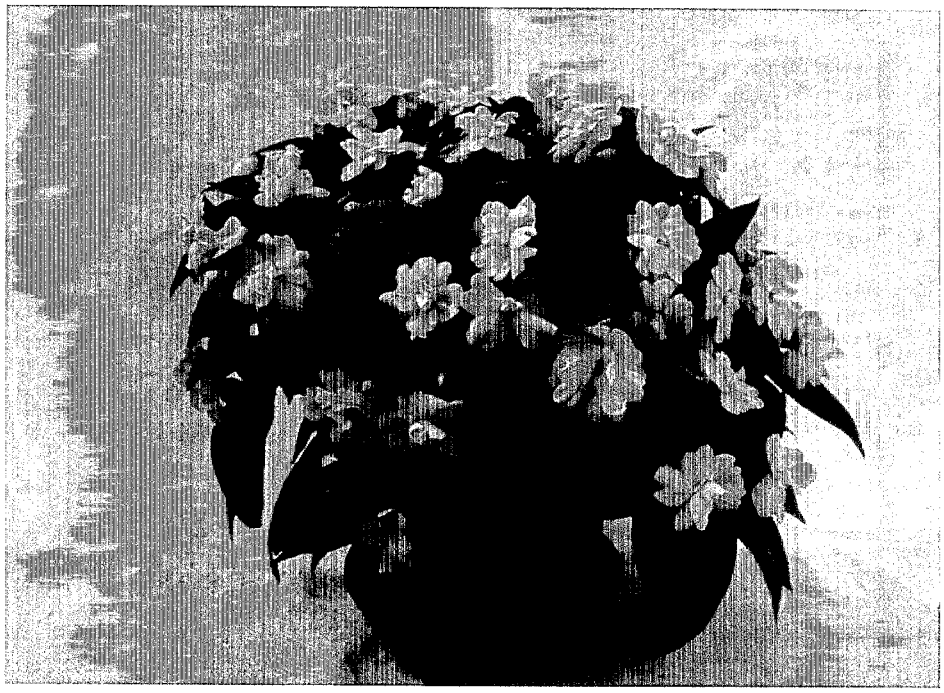
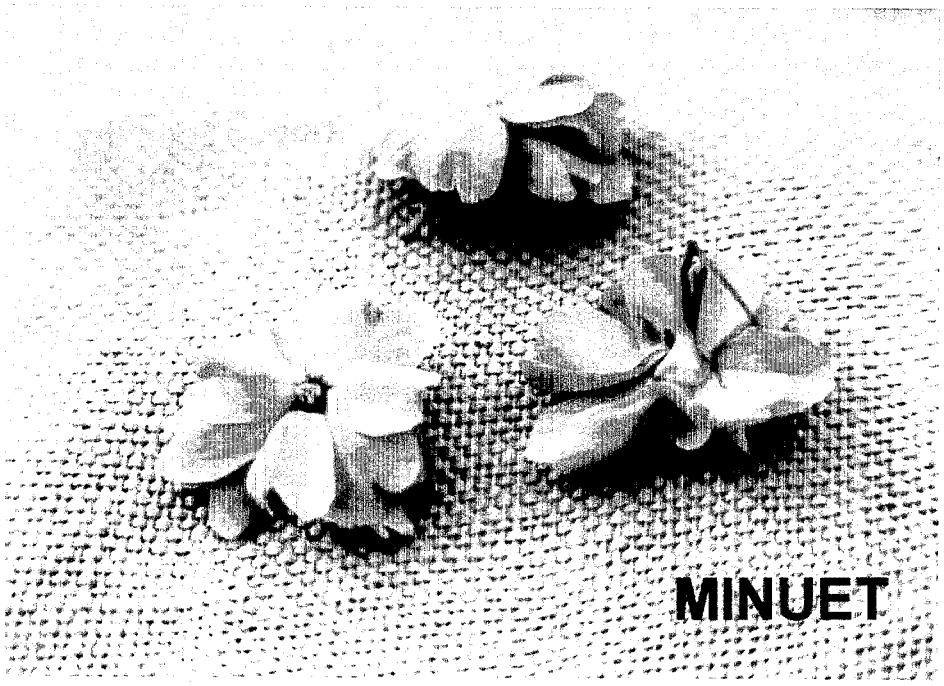
MINUET